(12) United States Patent
Heden et al.

(10) Patent No.: US 9,523,662 B2
(45) Date of Patent: Dec. 20, 2016

(54) COORDINATING INJECTOR-VALVE SWITCHING WITH PUMP-STROKE TIMING TO MITIGATE EFFECTS OF PRESSURE PULSES

(75) Inventors: John Heden, Hollis, NH (US); John Lamoureux, Franklin, MA (US); Miguel Soares, Norton, MA (US); Guo-Zhong Li, Westborough, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 860 days.

(21) Appl. No.: 13/511,691

(22) PCT Filed: Nov. 11, 2010

(86) PCT No.: PCT/US2010/056324
§ 371 (c)(1),
(2), (4) Date: Aug. 9, 2012

(87) PCT Pub. No.: WO2011/066111
PCT Pub. Date: Jun. 3, 2011

(65) Prior Publication Data
US 2012/0303167 A1   Nov. 29, 2012

Related U.S. Application Data (60) Provisional application No. 61/264,496, filed on Nov. 25, 2009, provisional application No. 61/297,913, filed on Jan. 25, 2010.

(51) Int. Cl.
*B01D 15/16* (2006.01)
*G01N 30/32* (2006.01)
(Continued)

(52) U.S. Cl.
CPC .............. *G01N 30/20* (2013.01); *G01N 30/24* (2013.01); *G01N 30/32* (2013.01); *B01D 15/163* (2013.01);
(Continued)

(58) Field of Classification Search
CPC ......... B01D 15/10; B01D 15/14; B01D 15/16; B01D 15/163; B01D 15/166; B01D 15/18; B01D 15/424; G01N 30/24; G01N 30/28; G01N 30/32; G01N 30/36; G01N 30/8696; G01N 30/22; G01N 30/20; G01N 2030/324; G01N 2030/326; G01N 2030/328; G01N 2030/8804; G01N 2030/201; G01N 2030/165
See application file for complete search history.

(56) References Cited

U.S. PATENT DOCUMENTS 3,982,432 A * 9/1976 Hammond ................. 73/152.45
4,767,279 A   8/1988 Dourdeville et al.
(Continued)

OTHER PUBLICATIONS

International Search Report and Written Opinion in counterpart international patent application No. PCT/US/10/56324, mailed on Jan. 31, 2011; 7 pages.

*Primary Examiner* — Katherine Zalasky
(74) *Attorney, Agent, or Firm* — Schmeiser, Olsen & Watts LLP (57) ABSTRACT

A liquid chromatography system includes an autosampler with an injector valve by which a sample at low pressure within a sample loop is introduced into a high-pressure solvent mixture stream. A solvent delivery system includes a pump in fluidic communication with the injector valve of the autosampler to deliver the solvent mixture stream thereto. The solvent delivery system further comprises a processor that calculates a number of strokes of the pump needed to deliver the solvent mixture stream to the injector (Continued)

valve of the autosampler. The processor counts strokes of the pump during delivery of the solvent mixture stream. In response to a stroke count equaling the calculated number of strokes, the processor signals the autosampler to switch the injector valve to introduce the sample to the solvent mixture stream during a pump transfer period within which the pump performs pressure control to compensate for a drop in pressure.

10 Claims, 6 Drawing Sheets

(51) Int. Cl.
| | | |
|---|---|---|
| *G01N 30/34* | (2006.01) | |
| *G01N 30/88* | (2006.01) | |
| *G01N 30/20* | (2006.01) | |
| *G01N 30/24* | (2006.01) | |
| G01N 30/86 | (2006.01) | |
| G01N 30/36 | (2006.01) | |

(52) U.S. Cl.
CPC ............ *B01D 15/166* (2013.01); *G01N 30/34* (2013.01); *G01N 30/36* (2013.01); *G01N 30/8696* (2013.01); *G01N 2030/322* (2013.01); *G01N 2030/326* (2013.01); *G01N 2030/8804* (2013.01)

(56) References Cited

U.S. PATENT DOCUMENTS

| | | | |
|---|---|---|---|
| 5,103,792 A | * | 4/1992 | Winkler et al. ............... 123/506 |
| 2006/0288803 A1 | * | 12/2006 | Weissgerber et al. ....... 73/865.8 |
| 2009/0062966 A1 | | 3/2009 | Pensak, Jr. et al. |

* cited by examiner

COORDINATING INJECTOR-VALVE SWITCHING WITH PUMP-STROKE TIMING TO MITIGATE EFFECTS OF PRESSURE PULSES

RELATED APPLICATIONS

This application claims the benefit of U.S. Provisional Application Ser. No. 61/264,496, filed Nov. 25, 2009, titled "Coordination of Injection-Valve Switching with Solvent Pump-Stroke Timing to Mitigate the Effects of Pressure Pulses," and of U.S. Provisional Application Ser. No. 61/297,913, filed Jan. 25, 2010, titled "Coordinating Injector-valve Switching with Pump-stroke Timing to Mitigate Effects of Pressure Pulses," the entireties of which provisional applications are incorporated by reference herein.

FIELD OF THE INVENTION

The invention relates generally to liquid chromatography systems. More specifically, the invention relates to reducing the effect of pressure pulses within the liquid chromatography system when injecting a sample into a solvent stream.

BACKGROUND

Chromatography is a set of techniques for separating a mixture into its constituents. In a liquid chromatography system, a pump takes in and delivers a high-pressure mixture of liquid solvents to an autosampler, where a sample within a sample loop awaits the arrival of the solvent stream. In an isocratic chromatography application, the composition of the liquid solvents remains unchanged, whereas in a gradient chromatography application, the solvent composition varies over time. After the mixture's arrival, to introduce the sample to the solvent stream, the autosampler switches an injector valve to place the sample loop in the path of the flowing mixture. The mobile phase, comprised of the sample dissolved in the solvent stream, then passes to a column of particulate matter, referred to as the stationary phase. By passing the mobile phase through the column, the various components in the sample separate from each other at different rates and thus elute from the column at different times. A detector receives the elution from the column and produces an output from which the identity and quantity of the analytes may be determined.

With high-pressure liquid chromatography systems, however, introducing a sample at low pressure into a high-pressure solvent stream can cause a significant pressure drop in the system. Moreover, aspirating the sample into the sample loop with air gaps in order to mitigate sample dispersion can exacerbate the pressure drop. Such pressure drops can produce undesirable deficits in delivered flow, thus negatively affecting the quality and reliability of the chromatographic outcome.

SUMMARY

In one aspect, the invention features a method for reducing pressure disturbances caused by introducing a low-pressure sample into a high-pressure solvent mixture stream, comprising calculating a number of strokes of a pump needed to deliver a solvent mixture to an injector valve of an autosampler. Strokes of the pump are counted during delivery of the solvent mixture. In response to a stroke count equaling the calculated number of strokes, the injector valve is opened to introduce the sample to the solvent mixture during a pump transfer period during which the pump performs pressure control to compensate for a drop in pressure.

In another aspect, the invention features a liquid chromatography system, comprising an autosampler including an injector valve by which to introduce a sample at low pressure within a sample loop to a high-pressure solvent mixture stream. A solvent delivery system includes a pump in fluidic communication with the injector valve of the autosampler to deliver the solvent mixture stream thereto. The solvent delivery system further comprises a processor that calculates a number of strokes of the pump needed to deliver the solvent mixture stream to the injector valve of the autosampler. The processor counts strokes of the pump during delivery of the solvent mixture stream. In response to a stroke count equaling the calculated number of strokes, the processor signals the autosampler to switch the injector valve to introduce the sample to the solvent mixture stream during a pump transfer period within which the pump performs pressure control to compensate for a drop in pressure.

In still another aspect, the invention features a method for reducing pressure disturbances in a liquid chromatography system caused by introducing a low-pressure sample into a high-pressure fluid stream. Control of a chromatographic injection sequence is transferred from an autosampler of the liquid chromatography system to a solvent delivery system of the liquid chromatography system. Calculated is a number of strokes of a pump of the solvent delivery system needed to completely deliver a pre-injection dwell volume to an injector valve of the autosampler. The solvent delivery system signals start of pre-injection operations of the autosampler and start of delivery of a solvent mixture stream. The solvent delivery system signals the autosampler to switch the injector valve to introduce a sample into the solvent mixture stream on a pump stroke boundary after the pump executes the calculated number of strokes.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Liquid chromatography systems described herein reduce pressure drops associated with injecting a low-pressure sample into a high-pressure solvent mixture stream delivered by a low-pressure mixing pump. In brief overview, to achieve this reduction, the solvent delivery system synchronizes sample injection with the mixing pump's transfer, a period during which a primary piston of the pump transfers a solvent stream to an accumulator piston. As used herein, the term "solvent stream" encompasses fluid streams comprised of unchanging (isocratic) and gradient solvent mixtures.

During each transfer, the pump automatically performs a pressure control process, which operates to compensate for any pressure drop resulting from the fluid transfer. When synchronized with sample injection, the pressure control process also operates to compensate for a pressure drop resulting from the introduction of the low-pressure sample into the high-pressure solvent stream. An example implementation of such synchronization is described in U.S. patent application Ser. No. 11/658,985, filed Oct. 3, 2008, titled "Devices, Systems and Methods for Flow-Compensating Pump-Injector Synchronization", the entirety of which application is incorporated by reference herein. As described in application Ser. No. 11/658,985, high-pressure mixing pumps run a pressure control process during a transfer period, which the autosampler synchronizes to coincide with sample injection. The autosampler can control the synchronization because these high-pressure mixing pumps are capable of performing a transfer "on-demand". When the sample is ready for injection, the autosampler requests the transfer and the pump responds by performing the transfer (with the attendant pressure control); this transfer occurs at the same time the autosampler switches the injector valve and introduces the low-pressure sample into the fluid stream. The pressure control process compensates for the pressure drop induced by the sample injection.

In contrast, low-pressure mixing pumps are incapable of performing a transfer on-demand. With low-pressure mixing pumps, once a pump stroke introduces a compositional mixture into the primary piston during intake, the pump is committed to delivering that compositional mixture on the next transfer. In order to be able to synchronize the transfer period with sample injection, control of the chromatographic injection sequence (i.e., when to start pre-injection operations of the autosampler relative to those of the solvent delivery system) are transferred from the autosampler to the solvent delivery system. Thus, instead of the autosampler forcing an on-demand piston-to-piston transfer, as is done with high-pressure mixing pumps, the low-pressure mixing pump forces an on-demand switch of the injector valve. More specifically, the solvent delivery system synchronizes the switching of the injector valve switch on a natural pump-stroke boundary, during a transfer period when the pressure control process automatically compensates for the pressure pulse.

To achieve this synchronization, the solvent delivery system takes into account the pre-injection dwell volume of the low-pressure mixing pump (i.e., the volume from the intake side of the pump to the injector valve of the autosampler). Before the foremost portion of the solvent stream can reach the injector valve, and, therefore, before injection can occur, the solvent delivery system must deliver this volume. Further, in order to take advantage of the pump's automatic pressure compensation, the solvent delivery system operates to synchronize full delivery of this volume (and sample injection) with a natural pump-stroke boundary.

As described herein, the solvent delivery system quantizes the pre-injection dwell volume into stroke volumes, and then calculates the number of pump strokes necessary to deliver the pre-injection dwell volume to the injector valve. This number is rounded up to the next stroke boundary (to ensure complete delivery of the pre-injection dwell volume). The solvent delivery system then counts pump strokes, instead of volume, in order to determine when to signal the autosampler to switch the injector valve.

Figure 1:
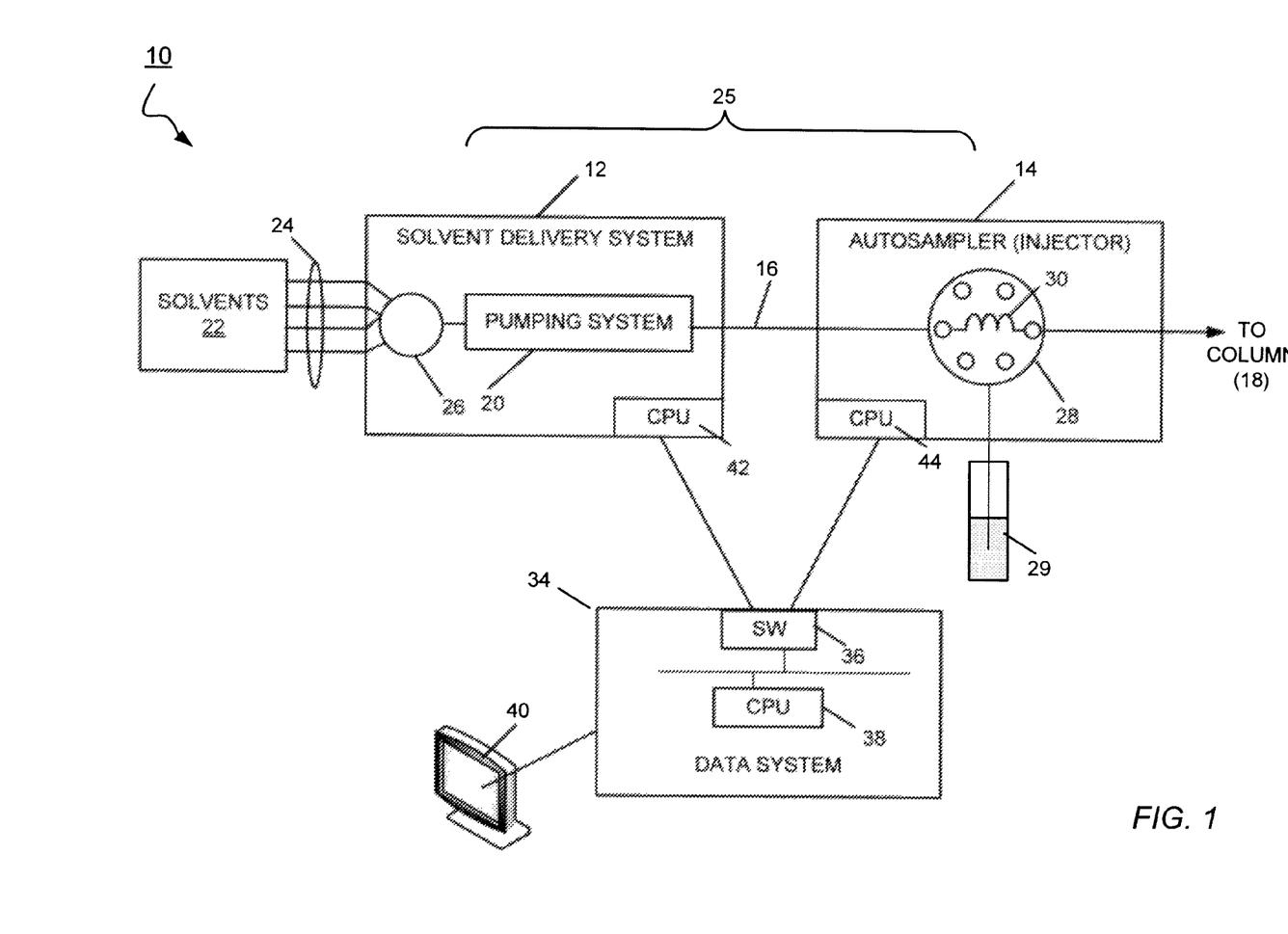
FIG. 1 is a functional block diagram of an embodiment of a liquid chromatography system.

FIG. 1 shows an embodiment of a liquid chromatography system 10 for separating a mixture into its constituents. The liquid chromatography system 10 includes a solvent delivery system 12 in fluidic communication with an autosampler 14 (also known as an injector or sample manager) through tubing 16. The autosampler 14 is in fluidic communication with a chromatographic column 18 of particulate matter. A detector (not shown), for example, a mass spectrometer, is in fluidic communication with the column 18 to receive the elution. Preferred liquid chromatography systems, and their various subsystems, are sold under various ACQUITY™ trademarks by Waters Corporation of Milford, Mass.

The solvent delivery system 12 includes a low-pressure pumping system 20 in fluidic communication with reservoirs 22 from which the pumping system 20 draws liquid solvents through tubing 24. In a low-pressure pumping system, the mixing of solvents occurs before the pump. The solvent delivery system 12 has a mixer 26 in fluidic communication with the solvent reservoirs 22 to receive various solvents in metered proportions. This mixing of solvents occurs in accordance with an intake profile, and produces a solvent (mobile phase) composition that remains unchanged (isocratic) or varies over time (gradient). The pumping system 20 is in fluidic communication with the mixer 26 to draw a continuous flow of solvent mixture therefrom for delivery to the autosampler 14. To draw and deliver the solvent mixture, the pumping system 20 can provide a flow rate in the range of 0.010 ml/min to 2 ml/min at 15,000 psi. Examples of pumping systems that can be used to implement the pumping system 20 include, but are not limited to, the ACQUITY UPLC Binary Solvent Manager, manufactured by Waters Corp. of Milford, Mass.

The autosampler 14 includes an injector valve 28 having a sample loop 30. The injector valve 28 can be a multi-port, multiple-position rotary valve of a type described in the aforementioned U.S. patent application Ser. No. 11/658,985. The autosampler 14 operates in one of two states: a load state and an injection state. In the load state, the position of the injector valve 28 is such that the autosampler 14 loads the sample 29 into the sample loop 30. In the injection state, the position of the injector valve 28 changes so that autosampler 14 introduces the sample in the sample loop 30 into the continuously flowing solvent stream from the solvent delivery system. The solvent stream thus carries the sample into the column 18. The pre-injection dwell volume 25 of this embodiment of chromatography system 10 extends from where the solvent mixture forms within the mixer 26 on the intake side of the pumping system 20 to the injector valve 28 of the autosampler 14.

Figure 2:
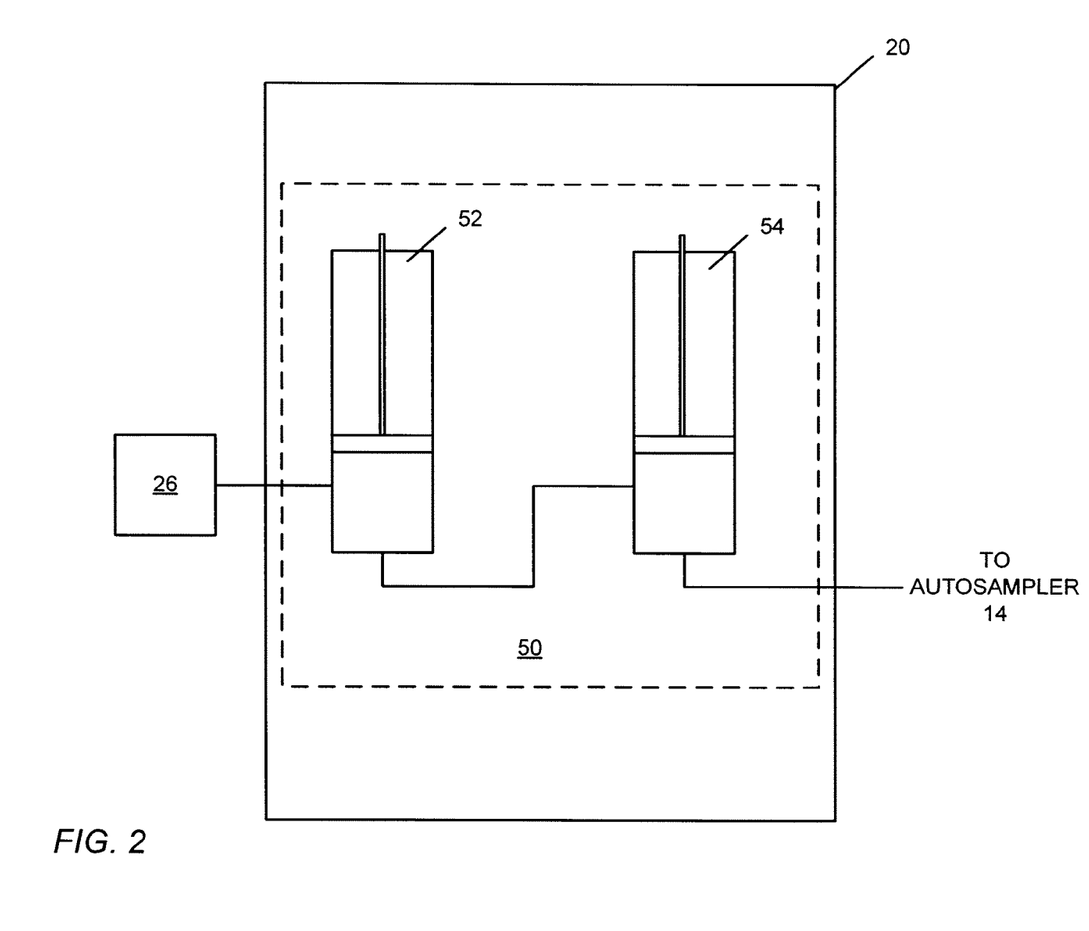
FIG. 2 is a block diagram of an embodiment of a pumping system.

Referring to FIG. 2, shown is an embodiment of a pumping system 20 having at least one two-piston pump 50, including a first piston head 52, referred to as the primary piston, in fluidic communication with a second piston head 54, referred to as the accumulator piston. The primary piston 52 intakes the solvent mixture from the mixer 26 and delivers the mixture to the accumulator piston 54. The accumulator piston 54 delivers the solvent mixture to the autosampler 14.

While the accumulator piston delivers the solvent stream at high pressure to the autosampler, the primary piston intakes new fluid from the mixer, and waits to refill the accumulator piston. When the accumulator piston completes its delivery stroke, the primary piston starts delivering its new fluid to the accumulator piston, which begins intake. This transfer of the solvent stream from the primary piston to the accumulator piston, referred to herein as a "transfer", occurs at high pressure, and continues until the accumulator piston is completely full and ready to resume delivery. When the transfer completes, the accumulator piston delivers the solvent mixture, while the primary piston intakes new fluid. This cycle, referred to herein as the "pump cycle", continuously repeats while the pump delivers the solvent stream to the autosampler. The duration of the pump cycle depends upon the stroke volume and delivered flow. In addition, to reduce or almost eliminate pressure disturbances in the pump caused by the transfer, the pump runs a pressure control process during the transfer period. An example implementation of a pump with two pistons coupled in series that runs a pressure control process is described in U.S. patent application Ser. No. 11/631,354, filed Oct. 22, 2007, titled High-Pressure Pump Control, the entirety of which patent application is incorporated by reference herein.

Figure 3:
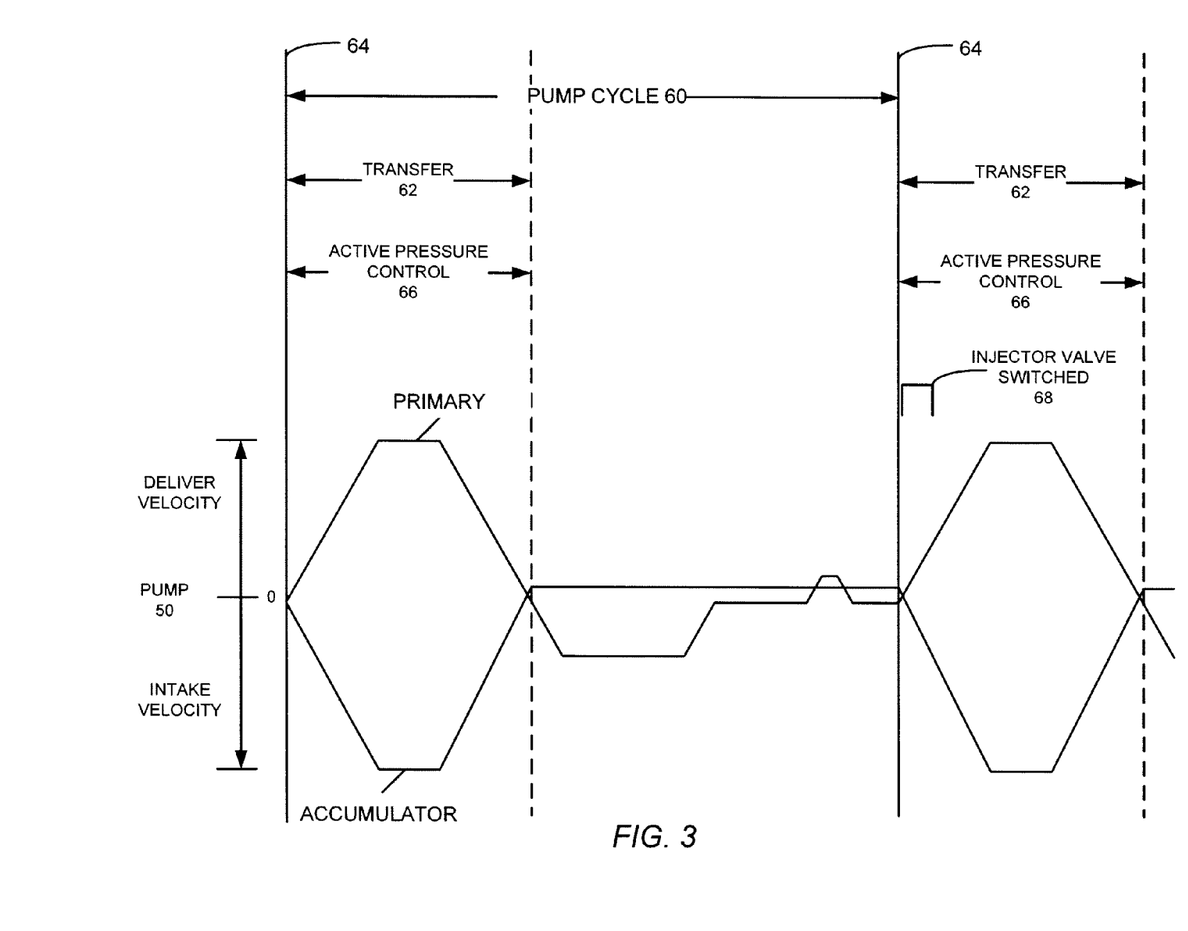
FIG. 3 is an embodiment of a timing diagram illustrating synchronization of switching the injector valve within a pump transfer period on a pump stroke boundary.

FIG. 3 shows an embodiment of a timing diagram illustrating the timing relationships during a pump cycle 60. During each pump cycle 60, the primary piston 52 executes a delivery stroke and an intake stroke, while the accumulator piston 54 executes an intake stroke and a delivery stroke. Vertical lines 64 represent pump stroke boundaries. The transfer between the primary piston 52 and the accumulator piston 54 occurs in an early portion 62 of the pump cycle 60 (where the primary piston delivers to an intaking accumulator piston). During this transfer period, the pump 50 automatically implements active pressure control 66. As described below, switching 68 of the injector valve occurs during a transfer period 62, while the pump is performing active pressure control 66.

Referring back to FIG. 1, the chromatography system 10 further includes a data system 34 that is in signal communication with the solvent delivery system 12 and the autosampler 14. The data system 34 has a processor 38 and a switch 36 (e.g., an Ethernet switch) for handling signal communication between the solvent delivery system 12 and autosampler 14, as described herein. Signal communication among the various systems and instruments is electrical, using wired transmission.

A host computing system 40 is in communication with the data system 34 by which a user can download various parameters and profiles (e.g., an intake velocity profile) to the data system 34. The downloaded parameters include method parameters for the solvent delivery system 12 and the autosampler 14 and injection parameters for the autosampler 14. Method parameters for the solvent delivery system 12 include, but are not limited to, a user-settable pre-injection (dwell) volume parameter and an initial flow rate parameter. Users may add different mixers and tubing, which affect the dwell volume; the pre-injection volume parameter provides a way to specify precisely the dwell volume of their system. A typical pre-injection dwell volume is 350-µl. Downloaded injection parameters include, but are not limited to, sample vial location and sample volume.

The solvent delivery system 12 has a processor 42 for controlling the flow rate of the pumping system and the solvent mixtures formation in accordance with downloaded method parameters. The processor 42 also calculates an amount of time and number of strokes needed to deliver the solvent mixture to the injector valve of the autosampler 14 based on the pre-injection dwell volume and flow rate.

The autosampler 14 has a processor 44 for controlling the loading and injection stages of operation in accordance with downloaded method and injection parameters. Before injection of the sample into the solvent stream can take place, the autosampler 14 has various pre-injection operations to perform. Among others, such operations include washing, purging, and aspirating the sample into the sample loop. The processor 44 calculates the amount of time for performing its pre-injection operations.

Figure 4A:
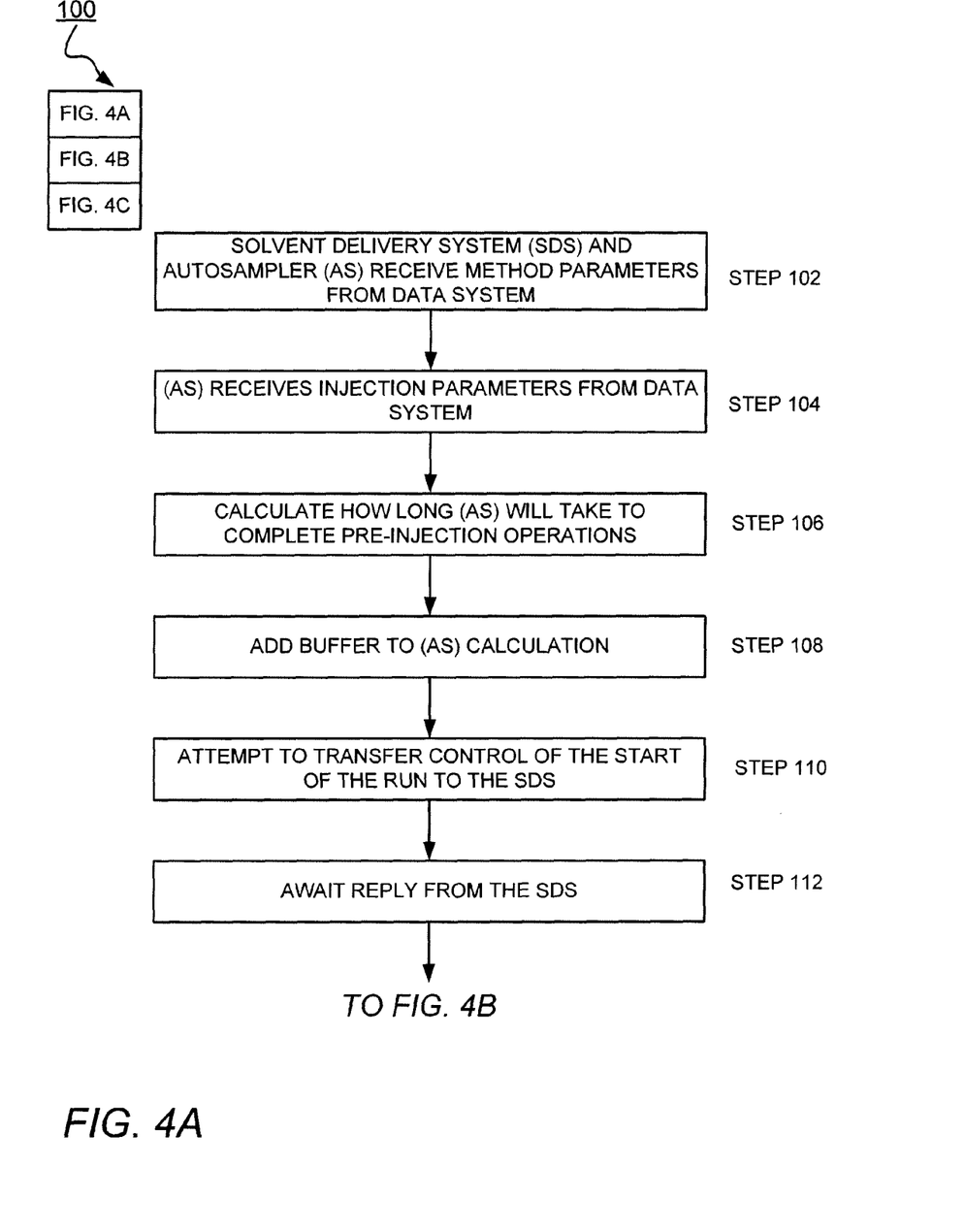
FIG. 4A, FIG. 4B, and FIG. 4C are flow diagrams of an embodiment of a process for synchronizing injector-valve switching with a transfer period of the pump.
Figure 4B:
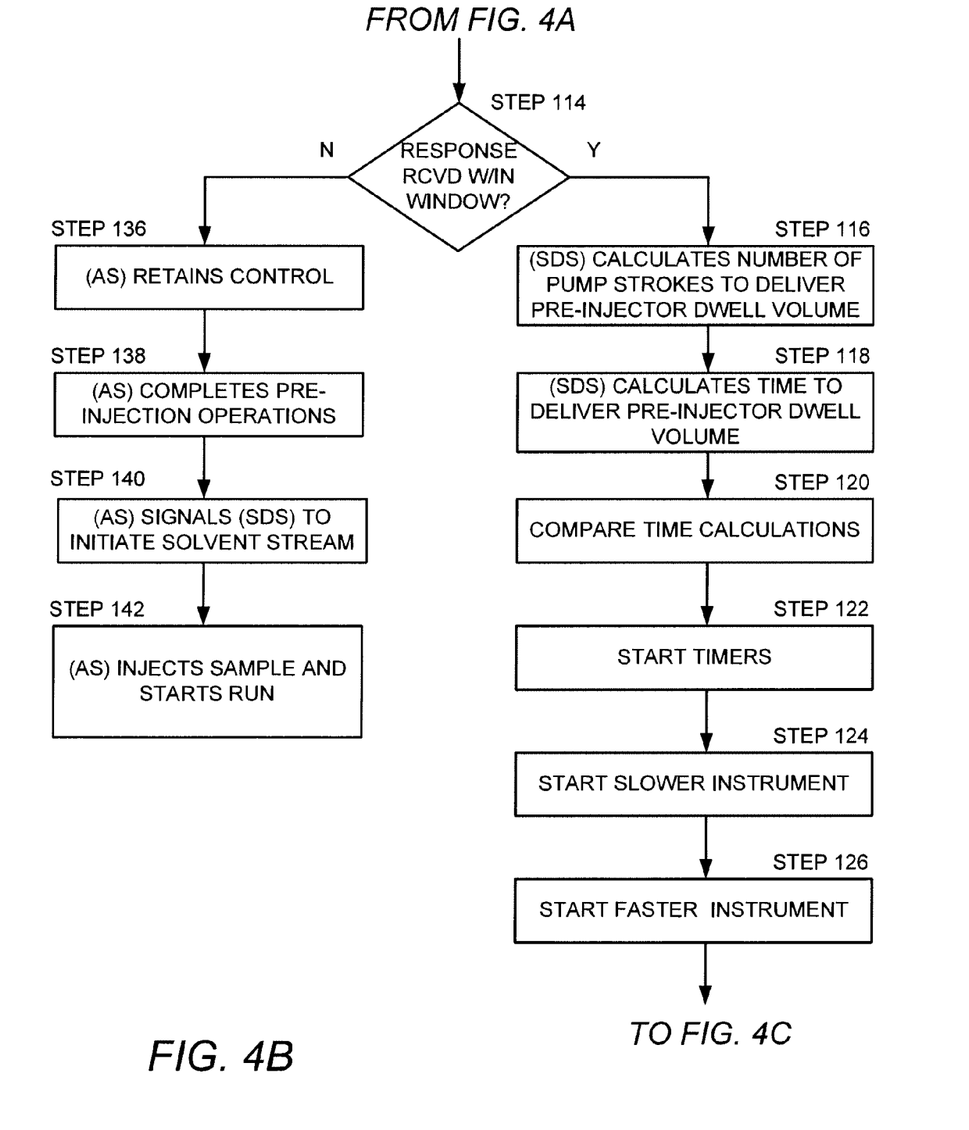
Figure 4C:
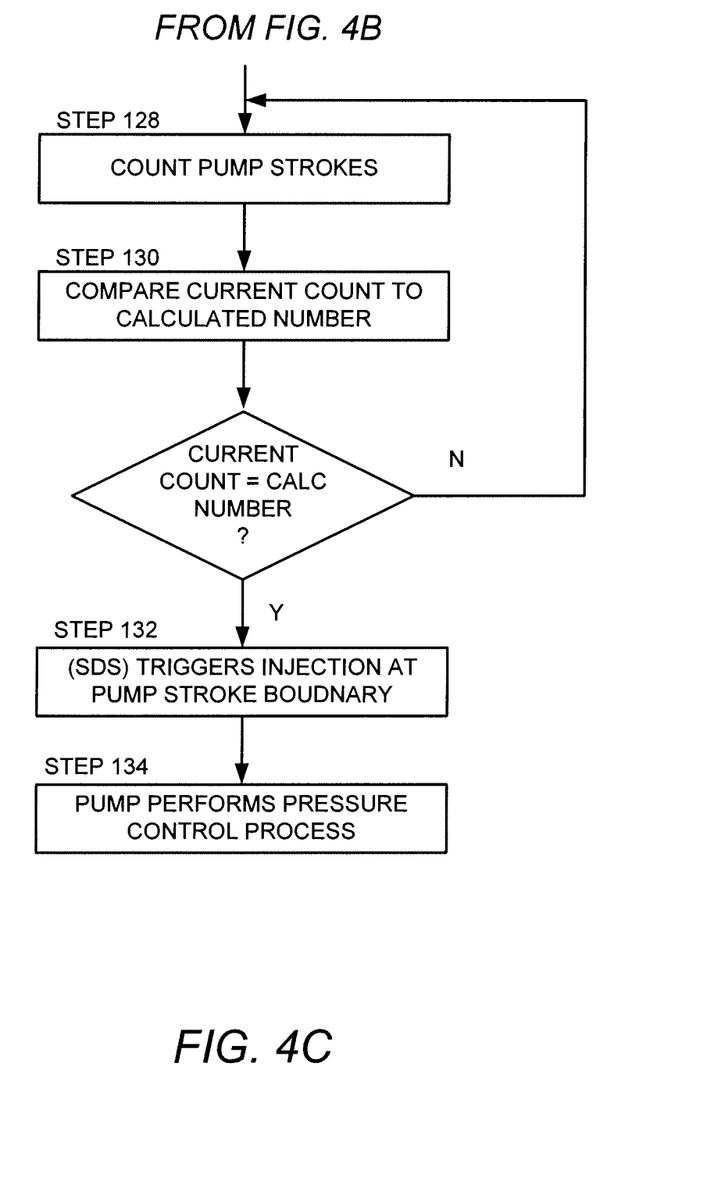

FIG. 4A, FIG. 4B, FIG. 4C show an embodiment of a process 100 for synchronizing the switching of the injector valve with pump-stroke timing in order to reduce the impact of pressure disturbances on pressure throughout the chromatography system 10. In the description of the process 100, reference is made also to items shown in FIG. 1.

At step 102, the solvent delivery system 12 and autosampler 14 receive their method parameters from the data system 34. The autosampler 14 also receives (step 104) its injection parameters from the data system 34. Based on an analysis of the injection parameters, the autosampler calculates (step 106) the amount of time needed to complete its pre-injection operations, for example, axes moves, sample draw, and air gap draw. A time buffer (or guard band) can be added (step 108) to the calculated time in order to ensure that the autosampler completes its pre-injection operations before the solvent stream arrives at the injector valve. In one embodiment, the time buffer is 5 seconds.

The autosampler attempts (step 110) to transfer responsibility for the chromatographic injection sequence to the solvent delivery system. In one embodiment, the autosampler sends the solvent delivery system a "delegate start run" message containing the time calculated for completing the autosampler's pre-injection operations. The autosampler then waits (step 112) a predefined maximum period (e.g., 500 ms) for the solvent delivery system to respond with a "delegate start run acknowledged" message.

If, at step 114, the autosampler does receives a "delegate start run acknowledged" message from the solvent delivery system within the defined period, the solvent delivery system 12 assumes responsibility for the chromatographic injection sequence. At step 116, the solvent delivery system calculates the number of pump strokes needed to deliver the solvent stream to the injector value by quantizing the pre-injection dwell volume into stroke volumes. For example, consider that upon each pump stroke, the solvent delivery system delivers 47 µl. For this stroke volume, delivering 400 µl of pre-injection dwell volume requires 9 pump strokes. The number of pumps strokes is rounded up to the next pump stroke to ensure delivery of the entire dwell volume. For example, if, instead, the stroke volume is 49 µl, the calculation is equal to 8.2 strokes (400/49), which is rounded up to 9 strokes.

At step 118, the solvent delivery system also calculates the amount of time needed to overcome its pre-injection dwell volume and deliver the solvent stream to the injector valve 28. The calculation is based on the initial flow rate and pre-injector volume method parameters. For example, consider that the solvent delivery system has a 400-µl pre-injection dwell volume, and a 0.6 ml/min flow rate, the solvent delivery system calculates that it will take 40 seconds to overcome the pre-injector dwell volume and deliver the solvent stream to the injector valve.

The solvent delivery system compares (step 120) the received calculation for completing autosampler's pre-injection operations with its own calculated time for delivering the solvent stream to the injector valve. The comparison serves to identify which of the two instruments (i.e., the solvent delivery system or the autosampler) is the slower instrument and which is the faster instrument. The solvent delivery system also calculates a difference in the two calculated times (herein, called delta t or $\Delta t$). For example, if the autosampler calculation is 40 seconds, and the solvent delivery system calculation is 75 seconds, then the autosampler is the faster of the two instruments and the delta t (Δt) is 35 seconds.

At step 122, two timers start running in the solvent delivery system. One timer controls when to start the slower instrument, and is referred to herein as the slow timer; the other timer controls when to start the faster instrument, and is referred to herein as the fast timer. The slow timer is set to start the slower instrument at a specific time (e.g., immediately) and the fast timer is set to start the faster instrument at a designated time after the slower instrument begins operations. That designated time is the calculated delta t (Δt), and is designed to cause the faster instrument to complete its pre-injection operations at the same moment the slower instrument completes its pre-injection operations.

At step 124, the slow timer starts the slower instrument, and at step 126, the fast timer starts the faster instrument. To direct the autosampler to start its pre-injection operations at the appropriate time, whether the autosampler is the slower or the faster instrument, the assigned timer sends the autosampler a "continue run" message. The timer assigned to the solvent delivery system, whether it's the slower or faster instrument, starts the solvent stream at its set time.

In the event the completion time calculated by the autosampler is equal to the solvent stream delivery time calculated by the solvent delivery system, both instruments start concurrently (delta t (Δt) is equal to 0), provided the autosampler's calculation includes a built-in time buffer to ensure sample injection occurs before delivery of the solvent stream.

When delivery of the solvent stream begins, the solvent delivery system keeps a count (FIG. 4C, step 128) of pump strokes and after each stroke compares the current count (step 130) to the calculated number of strokes needed to deliver the solvent stream to the injector valve. After the final stroke (i.e., the current count is equal to the calculated number of strokes), the solvent delivery system triggers (step 132) the injector valve to switch by sending the "start run" communication to the autosampler and all other instruments in the chromatography system. The start run message, sent to the autosampler and other instruments in the system, signals the actual injection event, where the injector valve transitions and data collection begins.

The transition of the injector valve occurs at the same time or slightly after the autosampler completes its pre-injection operations, thereby introducing the low-pressure sample into the high-pressure gradient fluid stream. In addition, injection occurs at the pump stroke boundary, during the transfer period in which the pump is actively compensating for pressure fluctuations by performing (step 134) the aforementioned pressure control process. The pump thus compensates for a pressure drop, reducing it dramatically.

By the time the solvent delivery system sends the "start run" message, the autosampler has presumably completed its pre-injection operation. In the event that the autosampler is still performing pre-injection operations at the time of receiving the start run message, for example, because of inaccurate completion estimations, the autosampler generates an error message and stops the run before the injection event can occur.

Alternatively, if, at step 114 (FIG. 4B), the autosampler does not receive a response within the defined period, the autosampler retains (step 136) control of the chromatographic injection sequence. For example, a method parameter received by the solvent delivery system may specify an initial condition of a 0 ml/min flow rate, signifying that the pumping system will not be flowing and, therefore, not delivering a gradient. In that event, the solvent delivery system does not send a "delegate start run acknowledged" message to the autosampler, and thus the autosampler retains responsibility for the chromatographic injection sequence. Sequential processing ensues: the autosampler starts and completes (step 138) its pre-injection operations and, then, after the sample is ready for injection, signals (step 140) the solvent delivery system to initiate the solvent stream. The autosampler then injects the sample and immediately afterwards sends (step 142) a "start run" message to all instruments in the chromatography system, including the solvent delivery system, to start the run.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects. All such forms may be generally referred to herein as a "system". Furthermore, aspects of the present invention may take the form of a computer program product embodied in one or more computer readable storage medium(s) having computer readable program code embodied thereon.

A computer readable storage medium may be any tangible medium that can contain, or store a program for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium include, but are not limited to, the following: a portable computer diskette, a hard disk, a random access memory (RAM), a read-only memory (ROM), an erasable programmable read-only memory (EEPROM, EPROM, Flash memory), an optical fiber, a portable compact disc read-only memory (CD-ROM), an optical storage device, a magnetic storage device, or any suitable combination of the foregoing.

Program code embodied on a computer readable medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

Aspects of the present invention are described below with reference to flowchart illustrations and/or block diagrams of methods, apparatus (systems), and computer program products according to embodiments of the invention. Each block of the flowchart illustrations and/or block diagrams, and combinations of blocks in the flowchart illustrations and/or block diagrams can be implemented by computer program instructions.

Computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Computer program instructions may also be stored in a computer readable storage medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the FIGS. illustrate the architecture, functionality, and operation of possible implementations of systems, methods, and computer program products according to various embodiments of the present invention. In this regard, each block in the flowchart or block diagrams may represent a module, segment, or portion of program code, which comprises one or more executable instructions for implementing the specified logical function(s). The functions noted in the blocks may occur out of the order noted in the FIGS. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the invention has been shown and described with reference to specific preferred embodiments, it should be understood by those skilled in the art that various changes in form and detail may be made therein without departing from the spirit and scope of the invention as defined by the following claims.

What is claimed is:

1. A method for reducing pressure disturbances caused by introducing a low-pressure sample into a high-pressure solvent mixture stream, comprising:
    calculating a number of strokes of a pump needed to deliver a solvent mixture stream through a pre-injection dwell volume from the pump to an injector valve of an autosampler;
    counting strokes of the pump during a delivery of the solvent mixture stream through the pre-injection dwell volume from the pump to the injector valve of the autosampler; and
    switching, in response to a stroke count equaling the calculated number of strokes, the injector valve to introduce the sample to the solvent mixture stream during a pump transfer period during which a primary piston of the pump transfers a solvent stream to an accumulator piston of the pump and during which the pump performs pressure control to compensate for a drop in pressure.

2. The method of claim 1, wherein calculating a number of strokes of a pump needed to deliver a solvent mixture stream through the pre-injection dwell volume from the pump to an injector valve of an autosampler includes rounding the number of strokes up to a next stroke boundary corresponding to a time when the primary piston of the pump begins a delivery stroke.

3. The method of claim 1, wherein the calculated number of strokes is determined from dividing the pre-injection dwell volume by the stroke volume.

4. The method of claim 1, wherein the switching of the injector valve occurs approximately simultaneously with when the autosampler completes one or more pre-injection operations and has the sample ready for injection.

5. The method of claim 1, further comprising transferring control of a chromatographic injection sequence from the autosampler to a solvent delivery system.

6. A method for reducing pressure disturbances in a liquid chromatography system caused by introducing a low-pressure sample into a high-pressure fluid stream, comprising:
    transferring control of a chromatographic injection sequence from an autosampler of the liquid chromatography system to a solvent delivery system of the liquid chromatography system;
    calculating a number of strokes of a pump of the solvent delivery system needed to completely deliver a pre-injection dwell volume from the pump to an injector valve of the autosampler;
    signaling, by the solvent delivery system, a start of pre-injection operations of the autosampler and start of delivery of a solvent mixture stream to the injector valve;
    signaling, by the solvent delivery system, the autosampler to switch the injector valve to introduce a sample to the solvent mixture stream on a next pump stroke boundary after the pump performs the calculated number of strokes;
    switching the injector valve during a transfer period of the pump during which a primary piston of the pump transfers a solvent stream to an accumulator piston of the pump, the switching of the injector valve occurring in response to the signaling of the autosampler by the solvent delivery system; and
    performing, by the pump, pressure control during the transfer period to compensate for a drop in pressure.

7. A method of claim 6, further comprising:
    determining the pre-injection dwell volume based on a stroke volume of the pump and wherein the calculating the number of strokes of the pump includes dividing the pre-injection dwell volume by the stroke volume.

8. The method of claim 6, wherein calculating a number of strokes of a pump needed to deliver the pre-injection dwell volume to the injector valve of the autosampler includes rounding the number of strokes up to a whole number corresponding to the next stroke boundary.

9. A method of claim 6, further comprising:
    keeping a count of strokes of the pump during a delivery of the pre-injection dwell volume; and wherein the signaling of the autosampler comprises signaling the autosampler to switch the injector valve in response to the stroke count equaling the calculated number of strokes.

10. The method of claim 6, wherein the switching of the injector valve occurs approximately simultaneously with when the autosampler completes pre-injection operations and has the sample ready for injection.

* * * * *